United States Patent [19]

Boesten

[11] 4,093,653

[45] * June 6, 1978

[54] PROCESS FOR THE PREPARATION OF OPTICALLY ACTIVE PHENYL GLYCINE AMIDE

[75] Inventor: Wilhelmus H. J. Boesten, Sittard, Netherlands

[73] Assignee: Stamicarbon, B.V., Geleen, Netherlands

[*] Notice: The portion of the term of this patent subsequent to Jul. 19, 1994, has been disclaimed.

[21] Appl. No.: 748,399

[22] Filed: Dec. 8, 1976

[30] Foreign Application Priority Data

Dec. 9, 1975 Netherlands .......................... 7514300

[51] Int. Cl.$^2$ ............................................ C07C 103/28
[52] U.S. Cl. ............................ 260/558 A; 260/559 A
[58] Field of Search ............ 260/558 A, 570.6, 584 R, 260/DIG. 7, DIG. 8, 559 A

[56] References Cited

U.S. PATENT DOCUMENTS

| | | | |
|---|---|---|---|
| 2,790,001 | 4/1957 | Purvis | 260/DIG. 8 |
| 3,705,900 | 12/1972 | Ryan | 260/DIG. 8 |
| 4,036,852 | 7/1977 | Boesten | 260/558 A X |

OTHER PUBLICATIONS

Suzuki et al., CA, 80:133826x (1974).
Watanabe et al., CA, 80:27470s (1974).
Sato et al., CA, 73:120879x (1970).
Günter, et al., CA, 55:14317a (1961).
Chibata et al., CA, 83:10843e (1975).
Sakieki et al., CA, 55:3449b (1961).
Hori et al., CA, 52:2056c (1958).
Betti et al., Ber., 41, pp. 2071–2073 (1908).

*Primary Examiner*—Daniel E. Wyman
*Assistant Examiner*—Thomas A. Waltz
*Attorney, Agent, or Firm*—Cushman, Darby & Cushman

[57] ABSTRACT

The invention is directed to a process for the separation of L-phenyl glycine amide from D-phenyl glycine amide by resolving a mixture containing the two optically active antipodes with an optically active acid, and racemizing the undesired antipode in the presence of a ketone and the optically active acid.

11 Claims, No Drawings

PROCESS FOR THE PREPARATION OF OPTICALLY ACTIVE PHENYL GLYCINE AMIDE

BACKGROUND OF THE INVENTION

The resolution of a mixture of D- and L-phenyl glycine amide by means of an optically active acid is described in co-pending U.S. patent application Ser. No. 623,928 filed Oct. 20, 1975, now U.S. Pat. No. 4,036,852 and U.S. patent application Ser. No. 733,851, filed Oct. 19, 1976. Both of these copending patent applications are by the inventor of the present application, and the entire specification and claims of each is hereby incorporated by reference in the present specification.

The invention relates to an improved process for preparing and isolating a particular optically active phenyl glycine amide by subjecting a mixture of L- and D-phenyl glycine amide to an improved optical resolution treatment. By means of the improved optical resolution treatment, it is possible to isolate improved yields of a desired optically active phenyl glycine amide. As used in the present specification, "a mixture of L- and D-phenyl glycine amide" means either a racemate of phenyl glycine amide, or mixtures of the racemate with either L-phenyl glycine amide or D-phenyl glycine amide.

Phenyl glycine amide can be hydrolized in a simple manner to form phenyl glycine, for example, by treatment with sulfuric acid, as described in the *Journal of the Chemical Society*, pages 393–97 (1966). Preparation of optically active phenyl glycine has been undertaken by an expensive procedure which includes treating DL-phenyl glycine with α-bromo-(D-camphor)-sulphonic acid to produce two diastereoisomer salts which are subsequently isolated. This prior procedure is described in *Berichte*, vol. 41, page 2073 (1908). The prior procedure is laborious and suffers the disadvantage that the α-bromo-(D-camphor)-sulphonic acid is expensive; the overall cost of the process is further increased because a certain amount of the camphor derivative is lost during the process.

Phenyl glycine amide can be prepared from the amino nitrile of phenyl glycine by hydrolyzing such as amino nitrile with an acid such as hydrochloric acid (see *Berichte*, vol. 14, page 1968), or by treating phenyl glycine alkyl esters with ammonia (see Journal of the American Chemical Soc., vol. 71 (1949), pages 78, 79). The phenyl glycine alkyl ester may be produced from phenyl glycine nitrile or phenyl glycine.

According to the two copending patent applications incorporated by reference above, it is possible to treat a mixture of L- and D-phenyl glycine amide with an optically active acid to form at least one of the possible diastereoisomer salts, and isolate a desired diastereoisomer salt. The present invention is an improvement inter alia in that the undesired antipode can be easily racemized in accordance with the process described in my copending U.S. patent application Ser. No. 748,398 filed concurrently herewith (incorporated by reference herein) and the resulting racemate subjected to resolution.

The optically active phenyl glycines which can be easily obtained from the resolved optically active phenyl glycine amides are valuable compounds.

For example, D-phenyl glycine is employed as a starting material for the preparation of α-amino benzyl penicillin. L-phenyl glycine provides a starting material for the sweetening agent L-asparagin-L-phenyl glycine alkyl ester.

SUMMARY OF THE INVENTION

According to the invention, a process has been discovered comprising an optical resolution of DL-phenyl glycine amide with the aid of an optical active acid and racemization of the undesired antipode.

It has been found that the racemization of the undesired optically active phenyl glycine amide can be very conveniently carried out in the presence of the optically active acid used to resolve the mixture without noticeable racemization of the optically active acid. Thus, in accordance with the invention the undesired antipode to be racemized need not be separated from the optically active acid used to resolve the mixture of L- and D-phenyl glycine amide.

It is therefore an object of the present invention to resolve a mixture of L- and D-phenyl glycine amide and improve the yield of one optically active phenyl glycine amide.

It is a further object of the present invention to obtain improved yields of a desired optically active phenyl glycine amide by isolating the desired optically active phenyl glycine amide and subjecting the undesired antipode to racemization and further resolution.

It is a further object of the present invention to carry out the racemization of the undesired optically active phenyl glycine amide in the presence of the optically active acid without noticeable racemization of the optically active acid, so that the undesired antipode to be racemized need not be separated from the optically active acid.

Surprisingly, it has been found that the objects of the present invention can be realized by preparing a mixture D- and L- phenyl glycine amide and an optical active acid; precipitating one antipode as diastereoisomer salt from a solution of that mixture; and racemizing in a solvent the other antipode from the mixture in the presence of a ketone and said optically active acid.

DETAILED DESCRIPTION OF THE INVENTION

The invention is directed to a process for the separation of L-phenyl glycine amide from D-phenyl glycine amide by treating a mixture containing the two optically active compounds with an optically active acid. The undesired antipode is racemized in the presence of the optically active acid used to resolve the mixture, and in the presence of a ketone.

Suitable optically active acids which may be used as resolving agents in the process of the present invention are optically active 2-pyrrolidone-5-carboxylic acid and optically active N-acetyl phenyl glycine. Resolution of a mixture of D- and L-phenyl glycine amide by treating the mixture with one of these optically active acids is fully disclosed in the two copending patent applications incorporated herein by reference. As those of ordinary skill in the art are aware, it is possible to resolve a mixture of an enantiomers by treating the mixture of an enantiomers with an optically active resolving agent. The reaction of an optically active acid according to the present invention with a mixture of D- and L-phenyl glycine amide results in the formation of diastereoisomer salts. Diastereoisomer salts have different physical properties and can be separated by the usual physical methods. In reacting an optically active acid according to the present invention with a mixture of D- and L- phenyl glycine amide, it is preferred to use a quantity of the optically active acid which is equivalent to the mixture of phenyl glycine amides present.

If optically active 2-pyrrolidone-5-carboxylic acid is used as the optically active acid in the practice of the present invention, there are several solvents in which the salt formed by the reaction of D-pyrrolidone carboxylic acid and D-phenyl glycine amide (D-D salt) is much less soluble than the salt formed by D-pyrrolidone carboxylic acid and L-phenyl glycine amide (D-L salt). These solvents include water, methanol, ethanol, isopropanol, dioxane, and mixtures of these compounds. Similarly, in these solvents the salt formed by the reaction of L-phenyl glycine amide with L-pyrrolidone carboxylic acid (L-L salt) is much less soluble than the corresponding salt formed by the reaction of D-phenyl glycine amide with the L-pyrrolidone carboxylic acid (D-L salt).

If N- acetyl phenyl glycine is used as the optically active acid in the process of the present invention, there are also several solvents in which the salt formed by the reaction of D-phenyl glycine amide with L-N-acetyl phenyl glycine (D-L salt) is much less soluble than the salt formed by the reaction of L-phenyl glycine amide with L-N-acetyl phenyl glycine (L-L salt). These suitable solvents include, for example, water, acetone, methyl ethyl ketone and mixtures of these solvents. Similarly, when these solvents are used, the slat formed by L-phenyl glycine amide and D-N-acetyl phenyl glycine (L-D salt) is much less soluble than the corresponding salt formed by the reaction of D-phenyl glycine amide with D-N-acetyl phenyl glycine (D-D salt).

In the practice of the present invention, a suitable optically active acid is chosen such that the desired diastereoisomer salt will be less soluble in the reaction mixture. Then the desired diastereoisomer salt can be readily isolated, for example, by filtration.

After the salt of the desired antipode is precipitated as diastereoisomer salt, the non-desired antipode is racemized in the presence of the optically active acid.

In the process according to the invention, it has been found that various ketones can be used to effect the racemization of the undesired antipode. For example, acetone, methyl ethyl ketone, and cyclohexanone may be used. The quantity of ketone can be varied within wide limits. A small amount of ketone, for example, about 0.1 mole of ketone per mole of phenyl glycine amide, is sufficient. The racemization treatment according to the invention can be carried out at a temperature between about 50° and about 100° C.

It is also possible, however, to use a larger amount of ketone and to have the ketone also serve as a solvent. In addition, solvents such as water, alcohols, benzene, toluene, chloroform and ethyl acetate can also be used as solvents in the racemization treatment.

It is a particular advantage of the process of the present invention that the racemization treatment of the non-desired antipode can be carried out in the presence of the same solvent in which the desired antipode is precipitated as diastereoisomer salt. Then, it is possible to carry out the resolution of the mixture and the racemization of the non-desired antipode together in a same amount of solvent. Hence, it is possible to convert a mixture of L- and D-phenyl glycine amide almost completely in one operation into the salt formed by the desired enantiomer of phenyl glycine amide with the optically active acid used. In the practice of the present invention, it is particularly preferred to use optically active N-acetyl phenyl glycine as the optically active acid, and it is particularly preferred to use acetone as the solvent.

The diastereoisomer salt obtained in the process according to the present invention can be reacted to remove the optically active acid component and free the desired antipode of phenyl glycine amide by methods which are known in the art. For example, the diastereoisomer salt can be separated into its components by treatment with an ion exchange resin. If the optically active acid used as a resolving agent in the practice of the present invention is optically active pyrrolidone carboxylic acid, the resulting diastereoisomer salt can be very conveniently separated into its components by first treating with a weakly basic ion exchange resin, e.g., Lewatit, and then treating with a strongly acidic ion exchange resin, e.g., Dowex 50. Alternatively, if the optically active acid used as a resolving agent in the practice of the present invention is optically active N-acetyl phenyl glycine, the desired diastereoisomer salt can be separated into its components by treatment with a strongly acidic ion exchange resin in the ammonium form, e.g., Dowex 50. Following treatment with the ammonium form of Dowex 50 the optically active phenyl glycine amide is bound to the ion exchange resin, while the optically active ammonium salt of N-acetyl phenyl glycine is separated and contained in the eluate. The eluate can be used, without further treatment, in the salt formation step. The optically active phenyl glycine amide bound to the ion exchange resin can be eluated with ammonia or with strong mineral acids.

The process according to the invention may be carried out in various ways by employing conventional procedures with the optical resolution of a mixture of optical antipodes by means of salt formation with acemization of the undesired antipode. The process will be further illustrated by the following examples, which are intended to be illustrative only and are meant to include all techniques equivalent thereto.

EXAMPLES

EXAMPLE I

In a flask equipped with a stirrer and a reflux cooler, a mixture of 6.0 g (0.04 mole) DL-phenyl glycine amide, 7.7 g (0.04 mole) L-N-acetyl phenyl glycine, and 60 ml acetone (1% vol. $H_2O$) is boiled at 58° C. for 15 hours, with stirring and reflux.

After cooling, the resulting crystal mass is recovered on a glass filter and twice washed on this filter with 10 ml of acetone in each washing. After drying at 50° C. and a pressure of 12 mm Hg, an amount of 12.8 g of D-L-salt is obtained, which corresponds to an efficiency of 90%. The term efficiency as used here refers to the percentage of the total quantity of salt which, theoretically, can be formed from the original amount of DL-amide if the non-desired enantiomer formed during the resolution is racemized completely.

2 g of the resulting D-L-salt is dissolved in 10 ml methanol, after which, during stirring, 1 ml (36%-wt.) hydrochloric acid and next 10 ml acetone are added. After filtration of the resulting D-phenyl glycine amide.HCl crystals these crystals are washed three times with 5 ml acetone. The specific rotation of the salt thus obtained is:

$[\alpha]_D^{20} = -102.5°$ (c = 0.8; water).

According to literature (see Beilstein 14, III, p. 1189) the specific rotation of D-phenyl glycine amide.HCl is:

$[\alpha]_D^{20} = -100.8°$ (c = 0.8; water).

8.5 g of the resulting D-L-salt (0.025 mole) is converted into D-phenyl glycine amide by dissolving the salt in 75 ml water and next passing the solution over 50 ml Dowex 50 ion exchanger in the ammonium form. After washing with 100 ml water the D-phenyl glycine is eluated with 100 ml ammonia water (4%-wt. NH₃). After evaporation to dryness in vacuo (12 ml Hg) at 30° C., an amount of 3.5 g D-phenyl glycine amide is obtained.

EXAMPLE II

In a flask equipped with a stirrer and a reflux cooler, 7.5 g (0.05 mole) DL-phenyl glycine amide, 6.4 g (0.05 mole) L-2-pyrrolidone-5-carboxylic acid, and 200 ml acetone (0.5%-vol. H₂O) are stirred, with reflux, at boiling temperature (about 58° C) for 20 hours.

After cooling to room temperature the resulting L-L-salt is recovered by filtration and twice washed on the filter, each time with 20 ml acetone.

The yield of L-L-salt is 11.9 g, which corresponds to an efficiency of 86%.

The specific rotation of the L-phenyl glycine amide.HCl prepared from the resulting L-L-salt analogously as in Example 1, is:

$[\alpha]_D^{20} = +97.5°$ (c = 0.8; water).

According to literature (see Beilstein 14, III, p. 1189), the specific rotation is:

$[\alpha]_D^{20} = +100.8°$ (c = 0.8; water).

EXAMPLE III

In a flask equipped with a stirrer and a reflux cooler, 7.5 g (0.05 mole) DL-phenyl glycine amide, 6.5 g (0.05 mole) D-pyrrolidone carboxylic acid, and 150 ml methyl ethyl ketone are heated, with stirring and reflux, at 80° C. for 4½ hours. After cooling, the mixture is stirred for another ½ hour at 25° C.

The resulting crystal mass is recovered on a glass filter and twice washed on the filter, each time with 25 ml methyl ethyl ketone. After drying, an amount of 11.6 g of D-D-salt is obtained, which means that the efficiency is 83.5%.

The specific rotation of the D-phenyl glycine amide.HCl, prepared from the resulting D-D-salt in a manner analogous to that described in Example I, is:

$[\alpha]_D^{20} = -100.1°$ (c = 0.8; water).

According to literature (see Beilstein 14, III, p. 1189) the specific rotation of this salt is:

$[\alpha]_D^{20} = -100.8°$ (c = 0.8; water).

Thus it is apparent that there has been provided in accordance with the invention, a process for the preparation of optically active phenyl glycine amide that fully satisfies the objects, aims, and advantages set forth above. While the invention has been described in conjunction with specific embodiments thereof, it is apparent that many alternatives, modifications, and variations will be evident to those skilled in the art in light of the foregoing description. Accordingly, it is intended to embrace all such alternatives, modifications, and variations as fall within the spirit and broad scope of the following claims.

What is claimed is:

1. A process for isolating an optically active form of phenyl glycine amide, from a mixture of D- and L-phenyl glycine amide, consisting essentially of:

preparing a mixture of D- and L-phenyl glycine amide and an optically active acid of the class consisting of 2-pyrrolidone-5-carboxylic acid and N-acetyl phenylglycine;

precipitating one antipode as diastereoisomer salt from a solution of said mixture;

and racemizing in a solvent the other antipode from the mixture in the presence of a ketone selected from the class consisting of acetone, methylethyl ketone and cyclohexanone and said optically active acid.

2. The process according to claim 1 wherein said optically active acid is N-acetyl phenyl glycine.

3. The process according to claim 1 wherein said optically active acid is 2-pyrrolidone-5-carboxylic acid.

4. The process according to claim 1 wherein said optically active acid is present in a quantity equivalent to the mixture of phenyl glycine amides present.

5. The process according to claim 2 wherein said optically active acid is L-N-acetyl phenyl glycine.

6. The process according to claim 2 wherein said optically active acid is D-N-acetyl phenyl glycine.

7. The process according to claim 1, wherein the racemization is carried out in the presence of a solvent in which the desired diastereoisomer salt precipitates.

8. The process according to claim 1 wherein the quantity of said optically active acid is in excess of equivalence to the mixture of phenyl glycine amides present.

9. The process according to claim 1 wherein said diastereoisomer separated from said mixture is separated by filtration.

10. The process according to claim 1 wherein said ketone is present in an amount of 0.1 mole of ketone per mole of phenyl glycine amide.

11. The process of claim 1 wherein said racemization treatment is carried out at a temperature between 50° and 100° C.

* * * * *